ary Examiner—John F. Lieberman

United States Patent [19]
Sadlowski et al.

[11] Patent Number: 4,909,953
[45] Date of Patent: Mar. 20, 1990

[54] PHOSPHATE BUFFER WASH FOR IMPROVED AMIDOPEROXYACID STORAGE STABILITY

[75] Inventors: Eugene S. Sadlowski, Cincinnati; Michael E. Burns, West Chester, both of Ohio

[73] Assignee: The Procter & Gamble Company, Cincinnati, Ohio

[21] Appl. No.: 213,413

[22] Filed: Jun. 30, 1988

[51] Int. Cl.⁴ .................... C11D 7/18; C11D 7/38; C11D 7/56
[52] U.S. Cl. ................. 252/99; 252/186.25; 252/186.26; 252/539
[58] Field of Search ............. 252/102, 98, 186.26, 252/186.25, 539

[56] References Cited
U.S. PATENT DOCUMENTS
4,686,063 4/1987 Burns .................... 252/102

FOREIGN PATENT DOCUMENTS
0037146 10/1981 European Pat. Off. .

Primary Examiner—John F. Lieberman
Assistant Examiner—John F. McNally
Attorney, Agent, or Firm—Kathleen M. Harleston; Donald F. Hasse; Thomas H. O'Flaherty

[57] ABSTRACT

Process for improving storage stability of amidoperoxyacid, comprising containing said amidoperoxyacid with a phosphate buffer solution at a pH between about 3.5 and 6 after synthesis of the amidoperoxyacid.

17 Claims, No Drawings

PHOSPHATE BUFFER WASH FOR IMPROVED AMIDOPEROXYACID STORAGE STABILITY

TECHNICAL FIELD

This invention relates to a process for improving the storage stability of an amidoperoxyacid, comprising contacting said amidoperoxyacid with a phosphate buffer solution at a pH between about 3.5 and 6 after synthesis of the amidoperoxyacid and before its incorporation into a final product. Chelants can optionally be added to the buffer to further improve the storage stability of the amidoperoxyacid.

BACKGROUND OF THE INVENTION

Organic peroxyacids are useful as fabric bleaching agents but are highly reactive compounds of limited storage stability. Storage stability refers to the extent to which the available oxygen (AvO) content of the peroxyacid is maintained over time.

Heretofore, generally three ways of improving storage stability of peroxyacids have been employed: chelants, pH control, and moisture control. The chelants combine with any metal ions present and thus prevent any decomposition of the peroxyacid which would be catalyzed by heavy metals. Seven references are representative: U.S. Pat. No. 4,170,453, Kitko, issued Oct. 9, 1979; U.S. Pat. No. 4,091,544, Hutchins, issued May 30, 1978; U.S. Pat. No. 4,100,095, Hutchins et al., issued July 11, 1978; U.S. Patent 4,126,573, Johnston, issued Nov. 21, 1978; U.S. Pat. No. 4,259,201, Cockrell, Jr. et al., issued Mar. 31, 1981; U.S. Pat. 4,325,828, Postlethwaite, issued Apr. 20, 1982; and European Patent Application No. 0068547, Bossu et al., filed June 9, 1982.

The preferred chelating stabilization system in these references is a mixture of 8-hydroxyquinoline or dipicolinic acid and an acid polyphosphate. Although chelants reduce or eliminate the problem of decomposition caused by heavy metals, they do not address the problem of decomposition of acid-sensitive peroxyacids caused by the acidic environment remaining after synthesis of the peroxyacid.

Several references suggest pH control as a way to optimize stability of bleach and/or detergent compositions. See European Patent Application No. 0176124, de Jong et al., published Apr. 2, 1986 (pH 3.5–4.5); European Patent Application No. 0201958, Meijer et al., published Nov. 20, 1986 (pH 4.1); U.S. Pat. No. 4,287,135, Stober et al., issued Sept. 1, 1981 (pH 2–6 and coating with reaction mixture); and European Patent Application No. 0200163, Jacobs et al., published Nov. 5, 1986 (pH 3–7). The last reference also includes a polymer coating of the bleach granule. All of these references except Stober et al. also include chelants.

European Patent Application No. 0212976, Coyne et al., published Mar. 4, 1987 teaches improved peracid stability through control of water levels during synthesis of peracid.

With an acid-sensitive peroxyacid such as an amidoperoxyacid, it is especially important that a way be found to make the peroxyacid stable for storage. Otherwise, the amidoperoxyacid, even with known storage stabilizers such as those described above, will decompose over time. It has been found that contacting the amidoperoxyacid with phosphate buffer at a pH between about 3.5 and 6, preferably between about 4 and 5, just after synthesis of the amidoperoxyacid, significantly slows this decomposition. Although this process is simple, it has heretofore not been used to stabilize peroxyacid. The amidoperoxyacid washed in phosphate buffer remains stable even when incorporated into an alkaline detergent composition, which is also surprising.

Amidoperoxyacids, or peroxyacids with a polar amide link in the hydrophobic chain, are described in U.S. Pat. No. 4,634,551, Burns et al., issued Jan. 6, 1987, and U.S. Pat. No. 4,686,063, Burns, issued Aug. 11, 1987. Such amidoperoxyacids have the following general formulas:

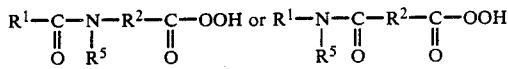

wherein $R_1$ and $R^2$ are alkyl(ene), aryl(ene) or alkaryl(ene) groups containing from about 1 to about 14 carbon atoms and $R^5$ is H or an alkyl, aryl, or alkaryl group containing from about 1 to about 10 carbon atoms.

Sulfone peroxyacids, which are generally more stable than amidoperoxyacids, are represented by the following formula:

wherein A and B are organic moieties bonded to the sulfur atom by a carbon atom and at least one of A and B containing at least one

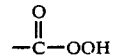

group bonded to a carbon atom. Sulfone peroxyacids are disclosed in European Patent Application No. 0267175, Dyroff et al., published May 11, 1988. In Example 4 of that application a methylene chloride solution of the sulfone peroxyacid was washed with phosphate buffer solution, then washed with water, partially evaporated and mixed with boric acid as a part of a series of steps.

It is an object of the present invention to provide a means of improving the storage stability of amidoperoxyacids.

It is also an object of the present invention to provide a means of improving amidoperoxyacid storage stability in a detergent composition.

SUMMARY OF THE INVENTION

This invention relates to a process for improving the storage stability of an amidoperoxyacid, comprising contacting said amidoperoxyacid with a phosphate buffer solution at a pH between about 3.5 and 6 after synthesis of the amidoperoxyacid and before its incorporation into a final product. Chelants can optionally be added to the buffer to further improve the storage stability of the amidoperoxyacid.

DETAILED DESCRIPTION OF THE INVENTION

Amidoperoxyacids are synthesized, then contacted with phosphate buffer solution at a pH between about 3.5 and 6, preferably between about 4 and 5. Conventional stabilizers known in the art can be, and preferably are, also employed. The stabilized amidoperoxyacid can then be agglomerated for use in a detergent composition or as a bleaching agent.

Amidoperoxyacids, or peroxyacids with a polar amide link in the hydrophobic chain, are described in U.S. Pat. No. 4,634,551, Burns et al., issued Jan. 6, 1987, and U.S. Pat. No. 4,686,063, Burns, issued Aug. 1987, both incorporated herein by reference.

Amidoperoxyacids herein have the following general formulas:

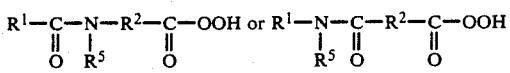

wherein $R^1$ and $R^2$ are alkyl(ene), aryl(ene) or alkaryl(ene) groups containing from about 1 to about 14 carbon atoms and $R^5$ is H or an alkyl, aryl, or alkaryl group containing from about 1 to about 10 carbon atoms. Preferred amidoperoxyacids are those having the following general formula:

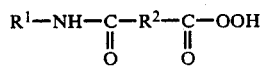

wherein $R^1$ is an alkyl group containing from about 6 to about 12 carbon atoms, and $R^2$ is an alkyl containing from 1 to about 6 carbon atoms.

The amidoperoxyacids most preferred herein are the monononylamide of peroxysuccinic acid ("NAPSA") and the monononylamide of peroxyadipic acid ("NAPAA"). Example I of U.S. Pat. No. 4,686,063 contains a description of the synthesis of NAPSA, from column 8, line 40 to Column 9, line 5, and NAPAA, from column 9, line 15 to column 9, line 65.

At the end of the amidoperoxyacid synthesis, the reaction is quenched with water, filtered, washed with water to remove some excess sulfuric acid (or other strong acid with which the peroxyacid was made), and filtered again.

The amidoperoxyacid wet cake thus obtained is contacted with a phosphate buffer solution at a pH between about 3.5 and 6, preferably between about 4 and 5. It has been found that if the pH of the amidoperoxyacid wet cake is raised too high, the amidoperoxyacid is dissolved, but if the pH is too low, the amidoperoxyacid is unstable. Without meaning to be bound by theory, it is believed that to stabilize the amidoperoxyacid, the strong acidity remaining from the sulfuric acid (or other strong acid) with which the peroxyacid is made must be neutralized without at the same time destroying the weak acid which is the peroxyacid. A buffer accomplishes this purpose. It has been determined that phosphate buffer, but not acetate or water washing, stabilizes the amidoperoxyacid. Since water washing to the same pH does not achieve the same effect as the phosphate buffer wash, it is theorized that some of the phosphate remains in the wet cake after contact with the phosphate buffer, which also helps storage stability. This is further borne out by the fact that phosphate buffer washing followed by water washing results in the peroxyacid having less stability than phosphate buffer washing alone.

The phosphate buffer is preferably orthophosphate or pyrophosphate in a concentration range of from about 0.01 M (moles/liter) to about 1 M. Most preferred is a 0.10 M solution of orthophosphates. These can be selected from the group consisting of $H_3PO_4$ (phosphoric acid), $NaH_2PO_4$ (monobasic sodium phosphate), $Na_2HPO_4$ (dibasic sodium phosphate), and $Na_3PO_4$ (tribasic sodium phosphate), so that the final solution has a pH of between about 3.5 and 6, preferably between about 4 and 5. Other salts such as potassium can be employed. Examples of phosphate buffer solution compositions can be found in *Buffers for pH and Metal Ion Control* by D.D. Perrin and Boyd Dempsey (Chapman & Hall, 1974).

There are several ways that the amidoperoxyacid can be contacted with the phosphate buffer solution. Preferably, the amidoperoxyacid wet cake is placed in enough of the phosphate buffer to cover it, and the combination is slowly stirred for a period of time sufficient to assure thorough contact with the wet cake. Approximately one hour for 20.0 g of wet cake in 400 ml of phosphate buffer (0.10 M, pH=4.75), for example, is an appropriate amount of time. Suction filtration is then preferably applied to remove the solution. The wet cake can then be air dried overnight. Conceivably, less phosphate buffer solution of a stronger concentration could be used. A 0.1 M phosphate buffer solution is preferred since it provides more volume and, when mixed with the wet cake, thorough contact and easier stirring than, for example, a 0.5 M solution.

Another preferred way of contacting the wet cake with the buffer is to pour the buffer over the wet cake and then apply vacuum filtration. In a plant, the filtered wet cake could be placed on a fluid bed for final drying before it is incorporated into the final detergent composition or bleaching agent.

The phosphate buffer wash should be done before the amidoperoxyacid has decomposed. The product has decomposed when there is so little amidoperoxyacid remaining that it is no longer an effective bleach. The activity of the amidoperoxyacid can be measured by the available oxygen. Generally, the higher the AvO is, the better the peroxyacid will bleach.

Other agents for storage stabilization or exotherm control can be added to the amidoperoxyacid before incorporation into the final product. It is preferred that boric acid, an exotherm control agent disclosed in U.S. Pat. No. 4,686,063, Burns, issued Aug. 11, 1987 and incorporated herein, be mixed with the preferred NAPSA (which has been washed in phosphate buffer) in about a 2:1 NAPSA:boric acid ratio. It is also preferred that the phosphate buffer washed NAPSA be mixed with appropriate amounts of dipicolinic acid and tetrasodium pyrophosphate, a chelating stabilization system (see Background section above). It is preferred that this mixture be formed into granules, dried, and used either separately or as part of a granular detergent composition.

The granules can be comprised of from about 1% to about 50% of the phosphate buffer washed amidoperoxyacid, preferably from about 10% to about 30% of NAPSA or NAPAA; from about 0.5% to about 25% of an exotherm control agent, preferably from about 5% to about 15% of boric acid; from 0 to about 10% of $C_{11-13}$ linear alkylbenzene sulfonate or $C_{14-15}$ alkyl sulfate, preferably from about 2% to about 7% of $C_{11-13}$ linear alkylbenzene sulfonate; from about 20% to about 70%, preferably from about 40% to about 60%, sulfate; and from 0 to about 20% of a chelating agent, preferably from about 0.02% to about 0.10% tetrasodium pyrophosphate and from about 0.05% to about 0.20% of dipicolinic acid.

Chelants can optionally be included in the phosphate buffer before contact with the wet cake. Without wishing to be bound by theory, it may be that adding the chelants in this way improves their effectiveness by more evenly distributing the chelants throughout the wet cake.

Examples of suitable chelants for use herein are: carboxylates, such as ethylene diamine tetraacetate (EDTA) and diethylene triamine pentaacetate (DTPA); polyphosphates, such as sodium acid pyrophosphate (SAPP), tetrasodium pyrophosphate (TSPP), and sodium tripolyphosphate (STPP); phosphonates, such as ethylhydroxydiphosphonate (Dequest® 2010) and other sequestering agents sold under the Dequest® trade name; and combinations of the above. Other sequestering agents for use herein are dipicolinic acid, picolinic acid, and 8-hydroxyquinoline, and combinations thereof.

It is preferred that the amidoperoxyacid washed in phosphate buffer be used in a detergent composition or as a separate bleaching agent. It is more preferred that the phosphate buffer washed amidoperoxyacid be incorporated into a granular detergent composition. It is most preferred that the amidoperoxyacid be NAPSA or NAPAA and be formed into granules (after the phosphate buffer wash and drying) which are then incorporated into a granular detergent composition.

Such detergent compositions comprise from about 0.5% to about 30%, preferably from about 1% to about 10%, of the amidoperoxyacid; from about 1% to about 40%, preferably from about 2% to about 30%, of detergent surfactants; and from about 5% to about 80%, preferably from about 10% to about 60%, of detergency builder. These detergent compositions can include any or all of the ingredients set forth n U.S. Pat. No. 3,936,537, Baskerville et al, incorporated herein by reference. Such components include color speckles, suds boosters, suds suppressors, antitarnish and/or anticorrosion agents, soil-suspending agents, soil-release agents, dyes, fillers, optical brighteners, germicides, alkalinity sources, hydrotropes, antioxidants, enzymes, enzyme stabilizing agents, perfumes, etc.

Appropriate ingredients are described in U.S. Pat. No. 4,686,063, column 4, line 4 to column 8, line 33, and U.S. Pat. No. 4,634,551, column 7, line 3 to column 11, line 33.

NAPSA which has been washed in phosphate buffer, filtered, granulated with boric acid and chelants, and incorporated into a granular detergent composition has significantly more available oxygen over time in product when compared to a control not washed in phosphate buffer (see Example II). This indicates that washing with phosphate buffer significantly improves amidoperoxyacid storage stability in a detergent composition.

The following examples are given to illustrate the parameters of and compositions within the invention. All percentages, parts and ratios are by weight unless otherwise indicated.

EXAMPLE I

A freshly-prepared sample of NAPSA (monononylamide of peroxysuccinic acid) wet cake was obtained which consisted of 6.7% water, 2.12% available oxygen (corresponding to 34.4% peroxyacid), and the rest (9.1%) unreacted starting material. This wet cake was the crude reaction product of NASA (monononylamide of succinic acid), sulfuric acid, and hydrogen peroxide which was subsequently quenched by addition to water followed by filtration, washing with distilled water, and final suction filtration to recover the wet cake. A 10% weight volume (w/v) slurry of wet cake (10 g wet cake solids in 100 ml of distilled water) had a pH of 3.15. Portions of the wet cake were then subjected to the following treatments. Phosphate buffers were made by mixing 0.10 M (moles/liter) solutions of $NaH_2PO_4$, $Na_2HPO_4$, and $Na_3PO_4$ to achieve the desired pH.

Sample #1 20.0 g of wet cake was air-dried overnight at room temperature. When dry, the sample pH (as a 10% w/v slurry in distilled water) was 2.96.

Sample #2 15.0 g of wet cake was washed with 1.0 liter of distilled water and then air-dried overnight at room temperature. When dry, the sample pH was 4.60.

Sample #3 20.0 g of wet cake was washed with 1.0 liter of phosphate buffer (0.10 M, pH=4.40) followed by 1.0 liter of distilled water and then air-dried overnight at room temperature. When dry, the sample pH was 4.59.

Sample #4 15.0 g of wet cake was washed with 1.0 liter of phosphate buffer (0.10 M, pH=4.50) and then air-dried overnight at room temperature. When dry, the sample pH was 4.49.

Sample #5 20.0 g of wet cake was placed in 400 ml of phosphate buffer (0.10 M, pH=4.75) and stirred for 1 hour after which it was recovered by suction filtration and air-dried overnight. When dry, the sample pH was 4.76.

The NAPSA samples were placed in open containers for storage stability testing at 80° F. (26.7° C.), 100° F. (37.8° C.), and 120° F. (48.9° C.). Stability was monitored by iodometric titration with sodium thiosulfate. Results are expressed below in terms of percent peroxyacid available oxygen (AvO) remaining as a function of time.

| Sample # | Wash | Temperature | Percent of Initial AvO Remaining After 12 Weeks |
|---|---|---|---|
| 1 | None | 80° F. | 40 |
|   |      | 100° F. | 37 |
|   |      | 120° F. | 2 |
| 2 | Water | 80° F. | 94 |
|   |       | 100° F. | 92 |
|   |       | 120° F. | 43 |
| 3 | Phosphate buffer then water | 80° F. | 100 |
|   |       | 100° F. | 99 |
|   |       | 120° F. | 70 |
| 4 | Phosphate buffer | 80° F. | 99 |
|   |       | 100° F. | 100 |
|   |       | 120° F. | 97 |
| 5 | Phosphate buffer-soaked | 80° F. | 98 |
|   |       | 100° F. | 98 |
|   |       | 120° F. | 96 |

Phosphate buffer stabilization of the peroxyacid does not occur only as the result of raising the wet cake pH. Washing the wet cake to a similar pH with water resulted in less stability after 12 weeks at 120° F. than when the phosphate buffer wash treatment was used (Sample #2 vs. Sample #4). Part of the beneficial effect of the phosphate buffer upon stability is apparently derived from residual amounts of buffer left in the peroxyacid wet cake after washing. Buffer washing followed by water washing resulted in peroxyacid having less stability than peroxyacid washed with buffer alone (Sample #3 vs. Sample #4).

EXAMPLE II

This example shows the improved storage stability of an amidoperoxyacid washed in phosphate buffer, filtered, granulated, and incorporated into a granular detergent composition.

Sample #1 of granulated NAPSA was prepared by combining the following:

80.00 g dried NAPSA wet cake (described in Example I)
31.31 g boric acid
25.05 g C13 linear alkylbenzene sulfonate paste
0.30 g dipicolinic acid
0.15 g tetrasodium pyrophosphate
123.58 g sodium sulfate
45.00 g water All ingredients were thoroughly mixed and then the granules
were formed by passing the mixture through a #18 Tyler mesh plastic sieve followed by air-drying overnight at room temperature. When dry, the granules prepared in this manner had a pH=4.21 (measured as a 10% weight volume slurry in distilled water).

Sample #2 of granulated NAPSA was prepared by combining all of the same ingredients in identical proportions with the exception that the NAPSA wet cake was first subjected to phosphate buffer treatment. 50.0 g of wet cake was added to a 1.0 liter of phosphate buffer (0.10 M, pH=4.75) and then stirred for 1 hour after which the NAPSA wet cake was recovered by suction filtration. Granulation was then carried out as for Sample #1. Sample #2 had a pH=4.23 after drying.

Portions of the granulated peroxyacid samples (16%) were combined with a phosphate detergent granule (84%) and placed in open containers at 80° F. (26.7° C.), 100° F. (37.8° C.), and 120° F. (48.9° C.) for storage stability testing.

The composition of the spray-dried phosphate detergent granule was:

| | Weight % |
|---|---|
| $C_{11-13}$ linear alkylbenzene sulfonate | 11 |
| $C_{14-15}$ alkyl sulfate | 11 |
| $C_{12-13}$ alkyl ethoxylate (6.5)* | 1 |
| Sodium tripolyphosphate | 36 |
| Sodium pyrophosphate and sodium acid pyrophosphate | 9 |
| Sodium silicate (2.0 ratio) | 4 |
| Sodium sulfate, moisture, and miscellaneous | 28 |
| Total | 100 |

*Alcohol and monoethoxylated alcohol removed.

Results are expressed below in terms of percent peroxyacid available oxygen (AvO) remaining as a function of time.

| Sample # | Wash | Temperature | Percent of Initial AvO Remaining After 12 Weeks |
|---|---|---|---|
| 1 | None | 80° F. | 97 |
| | | 100° F. | 95 |
| | | 120° F. | 8 |
| 2 | Phosphate buffer | 80° F. | 97 |
| | | 100° F. | 94 |
| | | 120° F. | 60 |

Thus the buffer treatment can increase in-product peroxyacid stability even when used in conjunction with other stabilizers such as dipicolinic acid and tetrasodium pyrophosphate.

EXAMPLE III

Wet cake containing the mononylamide of peroxyadipic acid (NAPAA) is prepared in the following manner. A weight of 50.0 g of the methyl ester of 6-nonylamino-6-oxocaproic acid is dissolved in 100 ml of methanesulfonic acid and the resulting solution is cooled in an ice bath. While stirring, 42.4 g of 70% $H_2O_2$ are added dropwise at a rate such that the temperature of the reaction mixture does not rise above 20° C.. After addition of the $H_2O_2$ is complete, the ice bath is removed and the reaction mixture is cooled in a freezer and then poured over ice. The solid reaction product is recovered as wet cake by filtration followed by water washing and final suction filtration. The wet cake is stabilized by addition to pyrophosphate buffer stabilizing solution in the ratio: 50 g wet cake/1.0 liter of solution. The pyrophosphate solution is 0.10 M, pH=5.00 (21.10 g $Na_2H_2P_2O_7$ +1.38 g $Na_4P_2O_7$+0.10 g Dequest® 2010 per liter) after which it is stirred for 15 minutes to 1 hour and recovered by suction filtration. The stabilized peroxyacid wet cake can then be dried or granulated.

EXAMPLE IV 50.0 g of NAPSA wet cake made as described in Example I above is stabilized by addition to 1 liter of phosphate buffer (0.10 M, pH=4.50), stirred for 1 hour, then recovered by suction filtration. The NAPSA is granulated by combining the stabilized wet cake with the following granule ingredients.

| | Weight % |
|---|---|
| NAPSA (solids) | 24.00 |
| NASA (solids, from wet cake) | 4.00 |
| Boric acid | 12.50 |
| $C_{13}$ linear alkylbenzene sulfonate (paste) | 5.00 |
| Dipicolinic acid | 0.12 |
| Tetrasodium pyrophosphate | 0.06 |
| Sodium sulfate | 54.32 |

The granules are formed by passage through a #18 Tyler mesh plastic sieve and are air-dried overnight.

The NAPSA granules are then admixed with a spray dried granular detergent composition to provide a finished bleach detergent composition having the following composition.

| | Weight % |
|---|---|
| $C_{11-13}$ linear alkylbenzene sulfonate | 8.0 |
| $C_{14-15}$ alkyl sulfate | 8.0 |
| $C_{12-13}$ alkyl ethoxylate (6.5)* | 0.2 |
| Sodium tripolyphosphate | 39.4 |
| Sodium carbonate | 12.3 |
| Sodium silicate (1.6 ratio) | 5.6 |
| NAPSA granules | 18.0 |
| Sodium sulfate, moisture, and miscellaneous | 8.5 |

*Alcohol and monoethoxylated alcohol removed.

What is claimed is:

1. A process for improving the storage stability of an amidoperoxyacid comprising contacting said amidoperoxyacid with a phosphate buffer solution; wherein said phosphate buffer solution and the buffered amidoperoxyacid have a pH between about 3.5 and 6, and wherein said phosphate buffer solution is comprised of orthophosphates or pyrophosphates or combinations thereof in a concentration range of from about 0.10M to about 1M.

2. A process for improving the storage stability of an amidoperoxyacid according to claim 1 wherein said amidoperoxyacid is contacted with said phosphate buffer for a sufficient period of time to assure through contact with the amidoperoxyacid, followed by filtration to remove the excess solution, and incorporation into a final product.

3. A process for improving the storage stability of an amidoperoxyacid according to claim 1 wherein said phosphate buffer solution is further comprised of chelants selected from the group consisting of carboxylates, polyphosphates, phosphonates, and mixtures thereof.

4. A process for improving the storage stability of an amidoperoxyacid according to claim 2 wherein said phosphate buffer solution is a 0.1M mixture selected from the group consisting of: $H_3PO_4$, $NaH_2PO_4$, $NaH_2HPO_4$, $Na_3PO_4$, and combinations thereof, so that the final solution has a pH of 5. A process for improving the storage stability of an amidoperoxyacid according to claim 1 wherein the phosphate buffer solution has a pH between about 4 and 5.

6. A process for improving the storage stability of an amidoperoxyacid according to claim 5 wherein the amidoperoxyacid is the mononylamide of peroxysuccinic acid.

7. A process for improving the storage stability of an amidoperoxyacid according to claim 5 wherein the amidoperoxyacid is the mononylamide of peroxyadipic acid.

8. A process for improving the storage stability of an amidoperoxyacid according to claim 1 wherein one or more chelating agents are added to the phosphate buffer solution before contact with the amidoperoxyacid.

9. A process for improving the storage stability of an amidoperoxyacid according to claim 7 wherein said mononylamide of peroxysuccinic acid is placed in enough phosphate buffer solution to cover it, stirred for a period of time sufficient to assure thorough contact, and then filtered.

10. A process for improving the storage stability of an amidoperoxyacid according to claim 7 wherein the phosphate buffer washed mononylamide of peroxysuccinic acid is mixed with one or more chelating agents and an exotherm control agent.

11. A detergent composition comprising from about 0.5% to about 30% of an amidoperoxyacid stabilized according to claim 1, and from about 1% to about 40% of detergent surfactants.

12. A detergent composition comprising from about 1% to about 10% of an amidoperoxyacid stabilized according to claim 5, from about 1% to about 40% of detergent surfactants, and from about 5% to about 80% of detergency buffer.

13. A detergent composition comprising from about 1% to about 10% of the mononylamide of peroxysuccinic acid stabilized according to claim 9, from about 15% to about 40% of detergent surfactants, and from about 5% to about 80% of detergency builder.

14. A detergent composition according to claim 11, comprising from about 2% to about 30% of detergent surfactants and from about 10% to about 60% of detergency builder.

15. A detergent composition according to claim 12, comprising from about 2% to about 30% of detergent surfactants and from about 10% to about 60% of detergency builder.

16. A granular detergent composition according to claim 11 further comprising a granule comprising from about 1% to about 50% of said amidoperoxyacid, from about 0.5% to about 25% exotherm control agent, from 0 to about 10% of $C_{11-13}$ linear alkylbenzene sulfonate or $C_{14-15}$ alkyl sulfate, from about 20% to about 70% of sulfate, and from 0 to about 20% of a chelating agent.

17. A granular detergent composition according to claim 11, further comprising a granule comprising from about 10% to about 30% of the mononylamide of peroxysuccinic acid or the mononylamide of peroxyadipic acid, from about 5% to about 15% of boric acid, from about 2% to about 7% of $C_{11-13}$ linear alkylbenzene sulfonate, from about 40% to about 60% sulfate, from about 0.02% to about 0.10% tetrasodium pyrophosphate, and from about 0.05% to about 0.20% of dipicolinic acid.

* * * * *

UNITED STATES PATENT AND TRADEMARK OFFICE
CERTIFICATE OF CORRECTION

PATENT NO.   : 4,909,953
DATED        : Mar. 20, 1990
INVENTOR(S)  : EUGENE S. SADLOWSKI  & MICHAEL E. BURNS

It is certified that error appears in the above-identified patent and that said Letters Patent is hereby corrected as shown below:

Column 5, line 62, "6.7%" should be -- 56.7% --.

Claim 4, Column 9, line 15 "pH of" should be -- pH of between about 3.5 and 6. --.

Claim 12, Column 10, line 11 "buffer." should be -- builder. --.

Claim 13, Column 10, line 15 "15%" should be -- 1% --.

Signed and Sealed this

Thirteenth Day of August, 1991

Attest:

HARRY F. MANBECK, JR.

Attesting Officer     Commissioner of Patents and Trademarks